United States Patent [19]

Demain et al.

[11] 4,307,192
[45] Dec. 22, 1981

[54] CELL-FREE SYNTHESIS OF DEACETOXYCEPHALOSPORIN C

[75] Inventors: Arnold L. Demain, Wellesley, Mass.; Toshio Konomi, Kobe, Japan; Jack E. Baldwin, Oxford, England

[73] Assignee: Massachusetts Institute of Technology, Cambridge, Mass.

[21] Appl. No.: 223,110

[22] Filed: Jan. 7, 1981

Related U.S. Application Data

[63] Continuation-in-part of Ser. No. 40,061, May 17, 1979, Pat. No. 4,248,966.

[51] Int. Cl.³ ............................................. C12P 35/00
[52] U.S. Cl. ...................................... 435/47; 435/926
[58] Field of Search ............................. 435/47, 43, 49

[56] References Cited

U.S. PATENT DOCUMENTS 3,847,742  11/1974  Higgens et al. .................... 435/47
3,979,260   9/1976  Nakao et al. ...................... 435/47
4,178,210  12/1979  Demain et al. .................... 435/47

Primary Examiner—Lionel M. Shapiro

Attorney, Agent, or Firm—Arthur A. Smith, Jr.; Anthony M. Lorusso

[57] ABSTRACT

A cell-free process for converting isopenicillin N, δ-(L-α-aminoadipyl)-L-cysteinyl-D-valine (hereinafter "LLD") and 6-substituted derivatives thereof to deacetoxycephalosporin C (DACPC) by the following reaction sequence:

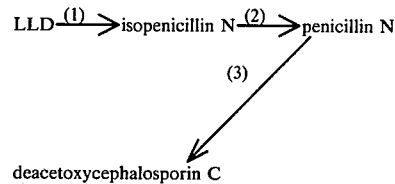

is disclosed. In addition to the starting material, the reaction system includes ATP and a fresh extract of *Cephalosporium acremonium* prepared and used in a manner to preserve the racemase agent or agents necessary for conversion of the isopenicillin N to penicillin N, a necessary intermediate step in the process.

9 Claims, No Drawings

CELL-FREE SYNTHESIS OF DEACETOXYCEPHALOSPORIN C

REFERENCE TO RELATED APPLICATION

This application is a continuation-in-part of copending U.S. application Ser. No. 40,061 filed May 17, 1979, U.S. Pat. No. 4,248,966, issued Feb. 3, 1981, entitled "Synthesis of Isopenicillin Derivatives in the Absence of Living Cells."

BACKGROUND OF THE INVENTION

1. Field of the Invention

This invention relates to a cell-free process for producing the antibiotic deacetoxycephalosporin C from isopenicillin N, LLD or their derivatives.

2. The Prior Art

Isopenicillin N is a water soluble β-lactam antibiotic having the formula:

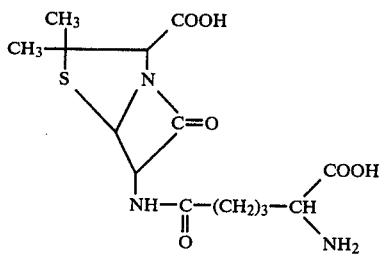

The aminoadipyl side chain is in the L-configuration in isopenicillin N. Penicillin N, also an effective antibiotic, has a structure identical to isopenicillin N except that the aminoadipyl side chain is in the D-configuration. Penicillin N and isopenicillin N have a number of properties in common but differ in their antimicrobial activity toward certain classes of microorganisms.

Deacetoxycephalosporin C (hereinafter referred to as DACPC) is useful as an antibiotic as such or as a starting compound for the production of cephalosporin antibiotics, such as cephalexin. DACPC is shown by the following formula:

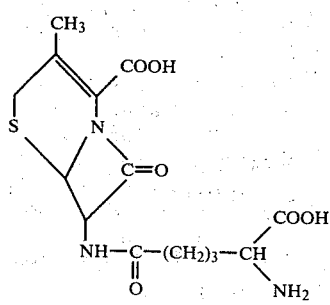

Cell-free syntheses of penicillins and the related antibiotic cephalosporins are known in the art. A cell-free cephalosporin synthesis, corresponding to step (3) in the reaction sequence of the present invention, is disclosed in U.S. Pat. No. 4,178,210 entitled "Acellular Synthesis of Cephalosporins", issued Dec. 11, 1979 to A. L. Demain et al. In U.S. Pat. No. 4,178,210 Demain et al teach that the process disclosed therein was successful in converting only the D-form, penicillin N, to a cephalosporin compound using the reactive system disclosed therein. Thus to utilize the teachings of U.S. Pat. No. 4,178,210 to convert isopenicillin N to a cephalosporin, a suitable process for converting isopenicillin N to its D-form isomer, penicillin N, must first be devised.

Accordingly an object of the present invention is to provide an integrated cell-free process for producing a cephalosporin compound from isopenicillin N or LLD.

These and other objects and features of the invention will be apparent from the following description of the preferred embodiments.

SUMMARY OF THE INVENTION

It has now been discovered that certain cell-free extracts of *Cephalosporium acremonium* contains a racemase agent or agents capable of converting isopenicillin N to penicillin N. In accordance with the present invention, cell-free extracts of *Cephalosporium acremonium* are prepared and used to catalyze reactions of isopenicillin N, 5-substituted derivatives of isopenicillin N and LLD much in the same manner as described in our copending application U.S. application Ser. No. 40,061, filed May 17, 1979, the teachings of which are incorporated herein by reference. However, in the present invention care is taken to preserve the racemase activity so that the catalyzed reaction of LLD (or its precursors) goes beyond the isopenicillin stage, through penicillin N, to form DACPC or a 6-substituted derivative thereof:

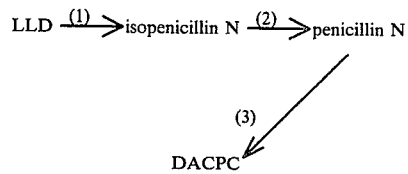

DACPC may be converted to cephalosporin C by standard techniques involving the hydroxylation of DACPC to deacetylcephalosporin C, followed by acetylation of the latter to cephalosporin C (e.g. Y. Fujisawa et al *Agr. Biol. Chem.*, 39 (1975), pp 2049–2055).

The agent responsible for the inversion by which an isopenicillin is converted to its penicillin isomer has been found to be quite labile, and is rendered inoperative by conventional extract preparation procedures. It is accordingly critical to prepare the extract in a manner such that the operability of the racemase is preserved. The preparation of cell-free extracts of *C. acremonium* for use in the present invention is designed to preserve the racemase agent or agents and differs from the preparation described in our aforementioned application U.S. Ser. No. 40,061 in the following particulars:

(1) fresh extracts, i.e. extracts which have never been frozen, are used;

(2) it is preferable to avoid treatment of the extract such as homogenization; and (3) when a phosphotransferase enzyme is employed in the synthesis, it is preferable that it be free of salt, e.g. free of $(NH_4)_2SO_4$.

Using isopenicillin N, or a 5-substituted derivative thereof as the starting material, DACPC and its 6-substituted derivatives are produced in accordance with the present invention as follows:

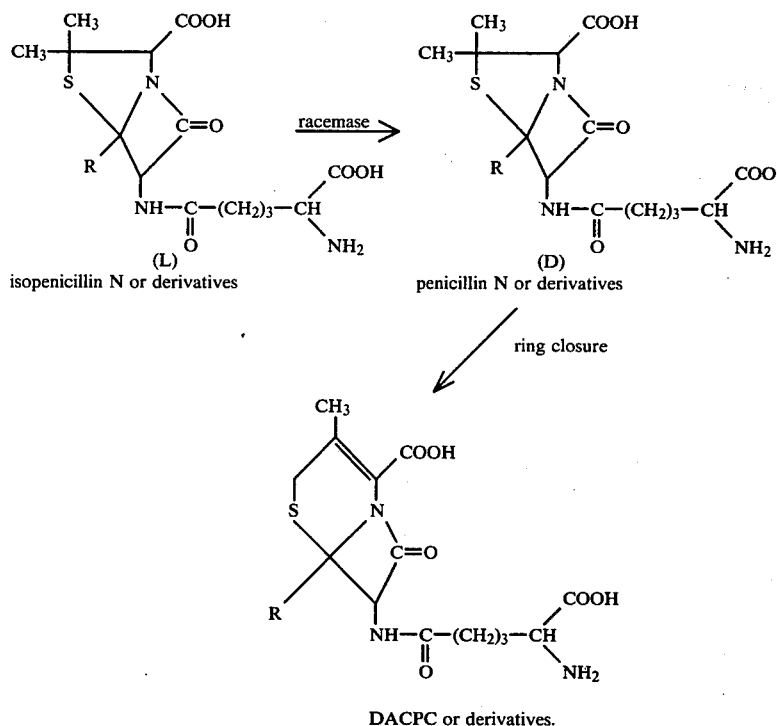

isopenicillin N or derivatives → penicillin N or derivatives

DACPC or derivatives.

Examples of other starting materials in the process of the invention include the following:

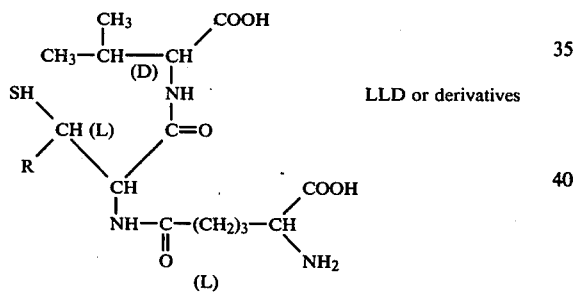

LLD or derivatives wherein R is hydrogen, methyl, ethyl, propyl or isopropyl or halogenated analogues of the foregoing radicals.

DESCRIPTION OF THE PREFERRED EMBODIMENTS

In accordance with the present invention, starting materials including isopenicillin N, 5-substituted derivatives thereof, or precursors thereof such as the aminoadipyl-cysteinylvaline tripeptide (LLD) are converted to ADCPC or 6-substituted derivatives thereof by a fresh, nonhomogenized cell-free extract of *C. acremonium* in the presence of ATP. The term "fresh", as used herein, refers to an extract that has never been frozen.

*C. acremonium* is a well known microorganism, and several strains are available from the American Type Culture Collection under names such as ATCC 20339 (Cephalosporium sp. strain F. 12), ATCC 14553 (*C. acremonium*) and *Acremonium strictum* ATCC 36255. In accordance with the present invention, the conversion may be carried out with "non-producing" mutants of ATCC 36255 for example, that designated M-0198. This mutant is blocked early, presumably in the formation of "LLD"; thus it does not produce antibiotics in the main culture medium. However, extracts prepared from this mutant can convert "LLD" to β-lactam antibiotics. Mutant M-0198 is available from the U.S. Department of Agriculture Collection as *Cephalosporium acremonium* NRRL-11418.

The preferred method of preparing the cell-free extract comprises lysing a protoplast pellet made from whole cells obtained from 40–70 hr. mycelia and treated with, e.g., Cytophaga lytic enzyme $L_1$ preparation and Zymolyase-5000. After treatment with the enzymes, the protoplast pellet suspension is centrifuged but not homogenized. The freshly-prepared extract is preferably subjected for a short time to sub-zero (Centigrade) temperatures (but not frozen). If the extract is frozen or homogenized, the enzyme system responsible for the critical optical inversion step from isopenicillin N to penicillin N is partially or completely inactivated. A second centrifugation enables separation of a supernatant liquid extract which may be used to catalyze the entire reaction sequence of the invention. Thus, if a suitable starting material is mixed with this fresh, nonhomogenized cell-free extract and ATP, a solution of DACPC, or 6-substituted derivatives thereof, is obtained.

The substances which are useful as starting materials include:

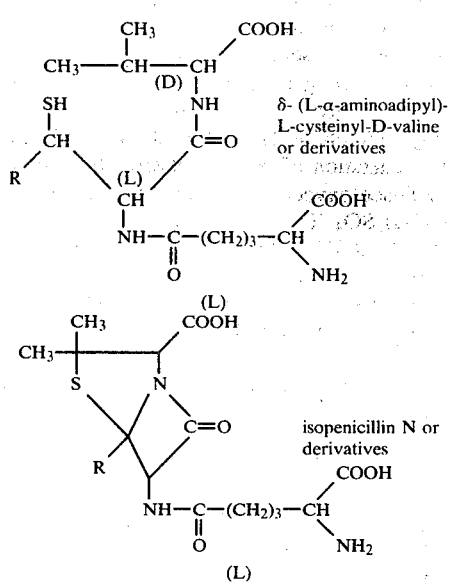

In the foregoing formulae, R can be hydrogen, methyl, ethyl, propyl, or isopropyl. If the starting material I is used, the extract will catalyze reactions to produce, in succession, II, then penicillin N and then DACPC or a 6-substituted derivative thereof. Likewise, if II is used, the extract will produce penicillin N and then DACPC or a 6-substituted derivative thereof. For further particulars of these reactions, see the aforementioned application Ser. No. 40,061. If the substituents on the 3 position of the thiazolidine ring are other than dimethyl, ring expansion does not occur.

In accordance with the invention, the extract effects the inversion of the aminoadipyl side chain from its L to its D conformation, thereby converting the isopenicillin N (or derivative) (II above) molecule to penicillin N (or derivative).

The addition of ATP, and/or ATP plus an ATP regeneration system, may increase the amount of product produced. The ATP regenerating system comprises a phosphate donor and a phosphotransferase enzyme. The preferred phosphate donor is phosphoenol pyruvate and its corresponding phosphotransferase enzyme, pyruvate kinase. However, it will be appreciated that other phosphate donor-phosphotransferase systems may also be used. These include but are not limited to phosphotransferases such as creatine kinase, acetate kinase, carbamate kinase, phosphoramidate kinase, arginine kinase, 3-phosphoglycerate kinase, and aspartate kinase, and corresponding phosphate donors such as creatine phosphate, acetyl phosphate, carbamyl phosphate, phosphoramidate, arginine phosphate, 1,3-diphosphoglycerate, and aspartyl phosphate. If an ATP regenerating system is used, it is preferable that the enzyme preparation employed be salt-free, e.g., free of $(NH_4)_2SO_4$, as otherwise the racemase enzyme in the extract is less active. Since the extract already contains some ATP, small quantities of antibiotic are produced even if no ATP is added to the reaction system. For the extract to synthesize the isopenicillin type molecule from LLD, it is also necessary that conditions which promote oxygen transfer be maintained in the reaction. However, the optical inversion step does not require a high degree of oxygen transfer.

The production of DACPC is detected with the aid of a mutant of either *Escherichia coli* (designated Ess and available on an unrestricted basis on request directed to the Department of Nutrition and Food Science, MIT, Cambridge, MA 02139) or *Pseudomonas aeruginosa* IFO 3080 (see Agr. Biol. Chem. 38(9), 1761-1712, 1974) which is supersensitive specifically to β-lactam antibiotics. The type of assay used is the conventional agar plate diffusion assay in which the agar (Antibiotic Medium No. 5, Difco Laboratories, Detroit, MI) is seeded with one of the above assay strains. Two types of plates are used. One contains 500 units of Difco penicillinase per ml agar and is used to assay DACPC since this molecule is stable to penicillinase. The other plate does not contain penicillinase and its assay represents the total assay of DACPC, penicillin N and isopenicillin N. The latter two are destroyed by penicillinase. The plates are incubated at 37° C. overnight and zones of inhibition are measured. Cephalosporin C is used as the standard to prepare the standard assay curve. DACPC is estimated in μg/ml since it is about as active as the standard cephalosporin C in the assay. Penicillin N plus isopenicillin N is determined by subtracting the DACPC assay value (in μg/ml) from the total assay in units/ml. One unit of penicillin N and/or isopenicillin N is that amount of antibiotic per ml which gives the same size zone as 1 μg/ml of cephalosporin C.

The invention will be further understood from the following non-limiting examples.

Preparation of Extract

A seed medium is prepared containing (per liter): 30 g corn steep liquor, 10 g glucose, 30 g starch, 5 g calcium carbonate. Forty ml of the medium adjusted to pH 6.8 are added to a 250 ml Erlenmeyer flask. One drop of methyl oleate is added from a 1 ml pipette and the flask is sterilized by autoclaving. After cooling, the seed flask is inoculated with 1 ml of *C. acremonium* suspension prepared by harvesting the mycelia from one slant culture with 5 ml of sterile water. The inoculated seed flask is incubated for 72 hours on a rotary shaker at 250 rpm with a 2 in. diameter orbit. The whole broth obtained is used to inoculate the main culture medium.

Main cultures of *C. acremonium* are incubated at 25° C. on the shaker at 250 rpm in 250 ml flasks containing 40 ml samples of a medium consisting of the ingredients set forth below. The specific *C. acremonium* strain used in these examples is a mutant of strain CW-19. Strain CW-19 was obtained from Eli Lilly and Co. and is available on an unrestricted basis under the designation *Acremonium strictum* ATCC 36255 from the American Type Culture Collection, Rockville, MD. The mutant, designated M-0198 is a strain which cannot produce penicillin N and cephalosporin C in fermentations and is available on an unrestricted basis from the Northern Regional Research Center, U.S. Dept. of Agriculture, Peoria, IL 61604 under the designation *Cephalosporium acremonium* NRRL-11418. It should be noted, however, that the invention is not limited to the use of specific mutant or strain of *C. acremonium*.

| Cephalosporium acremonium Main Culture Medium | |
|---|---|
| Sucrose | 36.0 g |
| Glucose | 27.0 g |
| $(NH_4)_2SO_4$ | 7.5 g |
| Oleic acid | 1.5 g |
| Salts #1 | 7.5 ml |
| Salts #2 | 135.0 ml |

| Cephalosporium acremonium Main Culture Medium | |
|---|---|
| L-Methionine | 3.0 g |

Water is added to these ingredients to 1 liter and the pH is adjusted to 7.3–7.5. Salts #2 is made up of a 20 g/l solution of ferrous ammonium sulfate.6H$_2$O. Salts #1 comprises a mixture of the ingredients set forth below dissolved in enough water to make 1.8 liters of solution.

| Salts #2 | |
|---|---|
| K$_2$HPO$_4$ | 208.0 g |
| KH$_2$PO$_4$ | 204.0 g |
| Na$_2$SO$_4$ . 10H$_2$O | 22.7 g |
| MgSO$_4$ . 7H$_2$O | 4.9 g |
| CaCl$_2$ . 2H$_2$O | 1.0 g |
| ZnSO$_4$ . 7H$_2$O | 0.4 g |
| MnSO$_4$ . H$_2$O | 0.4 g |
| CuSO$_4$ . 5H$_2$O | 0.1 g |

The mycelium harvested from six flasks after 40–70 hours of fermentation is filtered off and washed 2 times with 40 ml samples of distilled water. The damp-dry mycelium is resuspended in 40 ml of 0.05 M McIlvaine's citrate-phosphate buffer (pH 7.2) plus 0.01 M dithiothreitol and incubated for 1 hour at 28° C. with shaking at 150 rpm. After filtering and washing, the mycelium is resuspended in 40 ml of 0.05 M McIlvaine's buffer (pH 7.2) this time containing 1.0 M NaCl, 0.02 M MgSO$_4$, 160 mg of the lysing preparation Cytophaga lytic enzyme L$_1$, and 160 mg Zymolyase 5000 from Arthrobacter. Cytophaga lytic enzyme L$_1$ was obtained from BDH Chemicals, Poole, Dorset, U.K. In the U.S. it is sold by Gallard-Schlessinger Chem. Mgf. Corp., Carle Place, N.Y. 11514. The nature of the preparation of this enzyme is described in British Pat. No. 1,048,887. The lysing preparation was originally isolated from a culture medium of a microorganism temporarily designated L$_1$. This organism has been deposited in the National Collection of Industrial Bacteria in Aberdeen, Scotland, as N.C.I.B. 9497. Lytic enzyme L$_1$ has been described as having endo $\beta(1\rightarrow3)$ and endo $\beta(1\rightarrow4)$ glucanase activities (Biochemical Journal, Manners et al., Vol. 135, p. 11, 1973). Zymolyase-5000, (hereinafter zymolyase), was obtained from Kirin Brewery Co., Ltd., Takasaki, Gumma Pref, Japan. Zymolyase-5000 is an enzyme preparation produced by a submerged culture of *Arthrobacter luteus*. It lyses cell walls of viable fungi. As supplied by Kirin, Zymolyase-5000 contains the lytic enzyme and may also contain $\beta$-1,3 glucanase (EC3.2.1.39), mannanase, protease and acid phosphatase. The preparation of zymolyase has been described in *Archives of Biochemistry and Biophysics*, Kitamura et al., vol. 153, p. 403 (1972).

The suspension is incubated at 28° C. for 3 hours with shaking at 120 rpm and then centrifuged at 800 xg for about 10 minutes. The resulting pellet is washed twice with 20 ml of Tris buffer (pH 7.2, 0.05 M) containing 1.0 M sucrose, 0.01 M MgSO$_4$, and 0.01 M KCl.

Next, the protoplast pellet is cooled for 30 minutes to a temperature slightly above freezing. After 2 ml of tris buffer is added, the cold suspension is centrifuged at 1000 xg for 10 minutes. Approximately 2.5 ml of liquid cell-free extract is obtained per flask. Preparation of the extract in the manner set forth above results in preservation of the agent or agents present in whole cells which are responsible for the optical inversion of the aminoadipyl side chain. As will be shown in the examples, homogenization of the extract leads to lower production of deacetoxycephalosporin C. So does the presence of (NH$_4$)$_2$SO$_4$. The extract is then used to produce quantities of DACPC and its 6-substituted derivatives in accordance with the invention.

In all of the following tables, a zero (0) means below the limits of detection. A dash (—) means that the determination was not done at that time. If any zero time assay showed activity, this value was subtracted from all subsequent assay values.

EXAMPLE 1

This example illustrates a low degree of conversion of LLD to DACPC when a fresh extract is homogenized and the pyruvate kinase preparation contains ammonium sulfate.

A cell-free extract was prepared from a 52 hour culture of *C. acremonium* M-0198 as described above with the exception that homogenization of the protoplast lysate was carried out instead of the low temperature treatment. The reaction mixture (pH 7.2) was prepared with 5$\mu$ moles of adenosine triphosphate (ATP), 10 $\mu$ moles of phosphoenol pyruvate, 100 $\mu$g of pyruvate kinase in a (NH$_4$)$_2$SO$_4$ solution and 1 ml of cell-free extract. The substrate (LLD) was added to this reaction mixture over a range of concentrations and the mixture was incubated at 25° C. for five hours. Samples were removed during incubation and antibiotic activity was measured by an agar plate diffusion assay using cephalosporin C as a standard and a $\beta$-lactam supersensitive bacterial mutant as assay organism. The results show that a concentration of LLD as low as 50 $\mu$g/ml of reaction mixture can be converted to a detectable level of DACPC. Furthermore, the DACPC production increases as the concentration of the substrate is increased. The data also shows the transient accumulation of isopenicillin N and penicillin N during the reaction.

| Added LLD ($\mu$g/ml) | Penicillin N plus Isopenicillin N (units/ml) hours | | | | Deacetoxycephalosporin C ($\mu$g/ml) hours | | | |
|---|---|---|---|---|---|---|---|---|
| | 1 | 2 | 3 | 5 | 1 | 2 | 3 | 5 |
| 0 | 0 | 0 | 0 | 0 | 0 | 0 | 0 | 0 |
| 50 | 0.74 | 0.74 | 0.62 | tr | 0 | tr | tr | tr |
| 100 | 1.2 | 1.2 | 1.1 | 0.20 | 0 | tr | tr | 0.85 |
| 200 | 1.6 | 1.6 | 0.58 | 0.40 | 0 | tr | 0.85 | 0.90 |

EXAMPLE 2

A cell-free extract was prepared from a 36 hour culture of *C. acremonium* M-0198 as described above. The reaction mixture was prepared as in example 1 except that salt-free pyruvate kinase was used. Substrate, LLD or isopenicillin N, was added to the reaction mixture to final concentrations of 200 $\mu$g or 16 units, respectively. The following table shows that cells as young as 36 hours can convert LLD and isopenicillin N to DACPC.

| | Penicillin N and/or Isopenicillin N (units/ml) minutes | | | | | | | Deacetoxycephalosporin C (μg/ml) minutes | | | | | | |
|---|---|---|---|---|---|---|---|---|---|---|---|---|---|---|
| Additives/ml | 45 | 60 | 75 | 90 | 120 | 180 | 300 | 45 | 60 | 75 | 90 | 120 | 180 | 300 |
| none | 0 | 0 | 0 | 0 | 0 | 0 | 0 | 0 | 0 | 0 | 0 | 0 | 0 | 0 |
| 200 μg LLD | 14.0 | 14.0 | 14.0 | 14.0 | 14.0 | 10.8 | 8.0 | tr | tr | 0.38 | 0.48 | 0.60 | 1.1 | 1.3 |
| 16 units isopenicillin N | — | 15.7 | — | — | 12.3 | 10.8 | 7.3 | — | 0.30 | — | — | 0.48 | 0.60 | 0.70 |

EXAMPLE 3

Cell-free extract was prepared from a 60 hour culture of *C. acremonium* M-0198 as described in example 1. The reaction mixture was prepared as in example 1 except that salt-free pyruvate kinase was used. Substrate, LLD or isopenicillin N, was added to the reaction mixture to a final concentration of 200 μg/ml or 16 units/ml respectively. The results in the table below show that cells as old as 60 hours can convert LLD and isopenicillin N to DACPC.

| | Penicillin N plus Isopenicillin N (units/ml) minutes | | | | | | | Deacetoxycephalosporin C (μg/ml) minutes | | | | | | |
|---|---|---|---|---|---|---|---|---|---|---|---|---|---|
| Additive/ml | 30 | 45 | 60 | 75 | 90 | 120 | 180 | 30 | 45 | 60 | 75 | 90 | 120 | 180 |
| none | 0 | 0 | 0 | 0 | 0 | 0 | 0 | 0 | 0 | 0 | 0 | 0 | 0 | 0 |
| 200 μg LLD | 3.8 | 5.8 | 7.8 | 7.8 | 7.8 | 7.8 | 5.8 | tr | 0.60 | 1.6 | 2.2 | 2.8 | 3.5 | 4.0 |
| 16 units isopenicillin N | — | — | 14.0 | — | — | 11.2 | 8.6 | — | — | 2.0 | — | — | 3.1 | 5.0 |

EXAMPLE 4

Cell-free extract was prepared from a 52 hour culture of *C. acremonium* M-0198 grown in the main culture medium minus methionine. The cell-free extract and reaction mixture were prepared as described in example 1 except that salt-free pyruvate kinase was used. Substrate, LLD or isopenicillin N, was added to the reaction mixture to final concentrations of 200 μg/ml and 16 units/ml respectively. The table below shows that even when grown in the absence of methionine, the cells have the capacity to convert LLD and isopenicillin N to DACPC.

EXAMPLE 5

Cell-free extracts were prepared from a 52 hour culture as described above. The protoplast lysate was divided into two parts; one part was treated by homogenization, the other part by the cooling method described above. Reaction mixtures were prepared as in example 1 except that salt-free pyruvate kinase was used. Substrate, LLD or isopenicillin N, was added to final concentration of 200 μg/ml or 16 units/ml respectively. The following table shows that the extract prepared without homogenization produced much more DACPC from both substrates when compared to the homogenized preparation.

| Treatment of Extract | Additive/ Reaction Mixture | Penicillin N plus Isopenicillin N (units/ml) minutes | | | | | | | | Deacetoxycephalosporin C (μg/ml) minutes | | | | | | | |
|---|---|---|---|---|---|---|---|---|---|---|---|---|---|---|---|---|---|
| | | 15 | 30 | 45 | 60 | 75 | 90 | 120 | 180 | 15 | 30 | 45 | 60 | 75 | 90 | 120 | 180 |
| Fresh, Homogenized | none | 0 | 0 | 0 | 0 | 0 | 0 | 0 | 0 | 0 | 0 | 0 | 0 | 0 | 0 | 0 | 0 |
| | 200 μg LLD | 3.1 | 6.2 | 6.9 | 11.9 | 11.3 | 10.9 | 8.9 | 7.7 | 0 | tr | 1.3 | 2.2 | 2.8 | 3.2 | 3.6 | 4.8 |
| | 16 units isopenicillin N | — | — | — | 14.1 | — | — | 10.6 | 8.8 | — | — | — | 1.9 | — | — | 3.6 | 5.4 |
| Fresh, Chilled | none | 0 | 0 | 0 | 0 | 0 | 0 | 0 | 0 | 0 | 0 | 0 | 0 | 0 | 0 | 0 | 0 |
| | 200 μg LLD | 3.1 | 2.8 | 5.8 | 7.1 | 4.9 | 2.1 | 0.3 | 0.4 | tr | 3.2 | 4.8 | 7.0 | 9.2 | 12.0 | 13.8 | 13.8 |
| | 16 units isopenicillin N | — | — | — | 11.2 | — | — | 5.5 | 0.5 | — | — | — | 4.8 | — | — | 10.5 | 15.5 |

The cell-free extract prepared with no homogenization was frozen for 7 days at −20° C. It was then thawed and used to prepare a reaction mixture as described in example 1, except that salt-free pyruvate kinase was used. Substrate, LLD and isopenicillin N, was retested at final concentrations of 200 μg/ml and 10 units/ml respectively. The data in the table below show that DACPC production ability was destroyed by the 7 day freezing of the extract.

| | Penicillin N plus Isopenicillin N (units/ml) minutes | | | | | | Deacetoxycephalosporin C (μg/ml) minutes | | | | | |
|---|---|---|---|---|---|---|---|---|---|---|---|---|
| Additive/ml | 60 | 75 | 90 | 120 | 180 | 300 | 60 | 75 | 90 | 120 | 180 | 300 |
| none | 0 | 0 | 0 | 0 | 0 | 0 | 0 | 0 | 0 | 0 | 0 | 0 |
| 200 μg LLD | 3.9 | 3.9 | 3.9 | 3.5 | 3.1 | 1.9 | tr | 0.60 | 0.80 | 1.0 | 1.0 | 1.0 |
| 16 units isopenicillin N | 15 | — | — | 11.3 | 8.8 | 5.0 | 1.0 | — | — | 1.3 | 1.3 | 1.3 |

| Treatment of Extract | Additive/ml Reaction Mixture | Penicillin N plus Isopenicillin N (units/ml) minutes | | | | | | | | Deacetoxycephalosporin C ($\mu$g/ml) minutes | | | | | | | | |
|---|---|---|---|---|---|---|---|---|---|---|---|---|---|---|---|---|---|---|---|
| | | 15 | 30 | 45 | 60 | 75 | 90 | 120 | 180 | 300 | 15 | 30 | 45 | 60 | 75 | 90 | 120 | 180 | 300 |
| Chilled, Frozen 7 Days | 200 $\mu$g LLD | 0.60 | 1.4 | 3.1 | 4.2 | 4.2 | 4.2 | 4.2 | 2.2 | 0.88 | 0 | 0 | 0 | 0 | 0 | 0 | 0 | 0 | 0 |
| | 10 units isopenicillin N | — | — | — | 9.0 | — | — | 7.1 | 5.8 | 3.7 | — | — | — | 0 | — | — | 0 | 0 | 0 |

EXAMPLE 6

Cell-free extract was prepared from a 48 hour culture of C. acremonium M-0198 as described above. The extract was chilled and not subjected to homogenization. The standard reaction mixture was prepared as in example 1 except that the pyruvate kinase used was salt-free. A second reaction mixture, standard reaction mixture with salt-free pyruvate kinase to which $(NH_4)_2SO_4$ was added to a concentration of 22 mM, was also prepared. This concentration is the same as that present in reaction mixtures prepared with pyruvate kinase in 2.2 M $(NH_4)_2SO_4$ solution (i.e. not salt-free) as in example 1. Substrate, LLD or isopenicillin N, was added to the reaction mixtures to final concentrations of 200 $\mu$g/ml or 17.5 units/ml respectively. The data in the table below show that the conversions of LLD and isopenicillin are inhibited in the presence of $(NH_4)_2SO_4$.

zation agents (e.g. dimethylsulfoxide, benzene, toluene, Triton X-100) will be useable.

In order to transfer sufficient oxygen, the foregoing exemplary procedures require vigorous shaking. However, other methods of providing high oxygen transfer will be usable. For example, the use of oxygen enrichment will alleviate the vigorous shaking requirement.

Known methods may be employed to isolate the DACPC produced.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency are therefore intended to be embraced therein.

| | Additive/ml Reaction Mixture | Penicillin N plus Isopenicillin N (units/ml) minutes | | | | | | | | Deacetoxycephalosporin C ($\mu$g/ml) minutes | | | | | | | | |
|---|---|---|---|---|---|---|---|---|---|---|---|---|---|---|---|---|---|---|
| | | 15 | 30 | 45 | 60 | 75 | 90 | 120 | 180 | 300 | 15 | 30 | 45 | 60 | 75 | 90 | 120 | 180 | 300 |
| Standard Reaction Mixture | 200 $\mu$g LLD 17.5 units isopenicillin N | 3.7 — | 7.7 — | 13.7 — | 18.7 15.5 | 18.7 — | 18.7 — | 18.7 11.8 | 3.7 6.7 | | 0 — | tr — | tr — | 0.48 0.54 | 0.61 — | 0.76 — | 0.80 0.70 | 1.3 1.0 | 1.5 1.2 |
| | | | | | | | | 6.2 10.2 | | | | | | | | | | | |
| Standard Reaction Mixture and $(NH_4)_2SO_4$ | 200 $\mu$g LLD 17.5 units isopenicillin N | 0.85 — | 3.2 — | 6.9 — | 12.7 17.5 | 12.7 — | 12.7 — | 12.7 14.0 | 4.8 7.9 | | 0 — | 0 — | 0 — | tr 0 | tr — | tr — | tr 0 | tr 0 | tr 0 |
| | | | | | | | | 6.9 11.2 | | | | | | | | | | | |

From the foregoing, it will be obvious to those skilled in the art that various modifications in the above described process can be made without departing from the spirit and scope of the invention. For example, although ATP is probably necessary for the reaction, DACPC is produced whether or not an ATP regeneration system is added to the cell-free extract. Furthermore, although phosphoenol-pyruvate and pyruvate kinase are the preferred phosphate donor and phosphotransferase enzyme for use in regenerating ATP, it is clear that many other phosphate donors and transferase enzymes are operable and in fact that no ATP regeneration system at all necessarily be employed.

In addition to these modifications, it will be obvious to those skilled in the art that methods of producing the cell-free extract other than by treating the cells as disclosed herein will be possible. Specifically, it will be within the skill of those in the art to utilize other lysing enzymes, and indeed, other non-enzymatic methods of lysing the cell walls to produce the extract while preserving the racemase. Also, it is contemplated that enzymatically active fractions of the extract may be isolated, which fractions will show increased activity and be more productive of the antibiotics disclosed herein. Also it is contemplated that cells treated by permeabili-

We claim:

1. A process for producing deacetoxycephalosporin C or 6-substituted derivatives thereof comprising the steps of:

A. providing a starting material selected from the group consisting of:
  (a) a derivative of L-$\alpha$-aminoadipyl-L cysteinyl-D-valine of the formula:

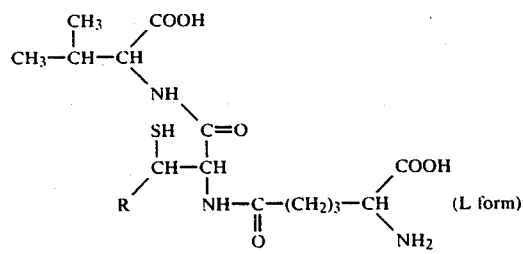

and (b) an isopenicillin derivative of the formula:

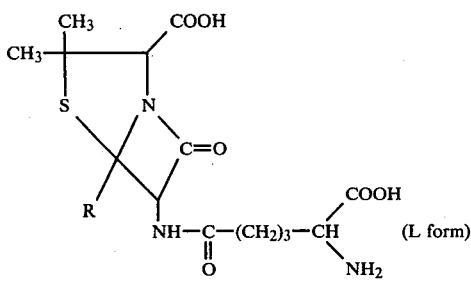

where R is selected from the group consisting of hydrogen, methyl, ethyl, propyl, and isopropyl;

B. preparing a cell-free extract of *Cephalosporium acremonium,* the preparation of the extract being such as to preserve the operability of an enzyme contained therein capable of inverting the aminoadipyl side chain of the penicillin molecule from the L to the D conformation;

C. contacting the extract and the starting material in a reaction zone while promoting oxygen transfer;

D. providing ATP as an energy source to said reaction zone; and

E. allowing a component of the extract to react with said starting material for a sufficient amount of time to produce a cephalosporin compound of the formula:

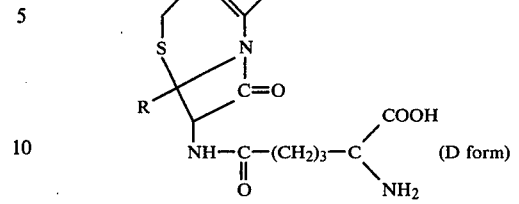

2. The process as set forth in claim 1 wherein R is hydrogen.

3. The process as set forth in claim 1 wherein the extract used in step C has not been homogenized or frozen.

4. The process as set forth in claim 1 wherein the ATP utilized is regenerated by a salt-free ATP regenerating system comprising a phosphate donor and a phosphotransferease enzyme.

5. The process as set forth in claim 4 wherein the phosphate donor is phosphoenol pyruvate and the phosphotransferase enzyme is pyruvate kinase.

6. The process as set forth in claim 1 wherein said cell-free extract is a fresh extract prepared by treating a *Cephalosporium acremonium* culture with a lysing enzyme.

7. The process as set forth in claim 6 wherein said cell-free extract is made by treating *Cephalosporium acremonium* cells with endo $\beta(1\rightarrow 3)$ glucanase, endo $\beta(1\rightarrow 4)$ glucanase, and zymolyase.

8. The process as set forth in claim 1 wherein oxygen transfer is promoted by shaking the reaction components in the reaction zone.

9. The process as set forth in claim 1 wherein sucrose and trace concentrations of KCl and $MgSO_4$ are included in the reaction system, and the system is buffered to about pH 7.2.

* * * * *